United States Patent
Sakata et al.

[11] Patent Number: 4,604,241
[45] Date of Patent: Aug. 5, 1986

[54] 9-DESOXO-9-HYDROXY-PHEOPHORBIDE DERIVATIVES AND ALKALINE SALTS THEREOF

[76] Inventors: Isao Sakata, 1766-4, Obira, Kasaoka City, Okayama Pref.; Susumu Nakajima, 4-4-34, Gojo, Midorigaoka, Asahikawa City, Hokkaido; Koichi Koshimizu, 385-10 Horensan soinishi cho, Nara City, Nara Pref.; Natsuki Samejima, A-42, Idai Shukusha, 3-3 Nijo, Midorigaoka, Asahikawa Ci; Kazumi Inohara, 3-9-7 Mikado cho, Fukuyama City, Hiroshima Pref.; Hiroyuki Takata, 2098 Satomi, Satosho cho, Asakuchi gun, Okayam Pref., all of Japan

[21] Appl. No.: 664,375

[22] Filed: Oct. 24, 1984

[30] Foreign Application Priority Data

Oct. 24, 1983 [JP] Japan .................. 58-198934

[51] Int. Cl.$^4$ .......................... C07D 487/22
[52] U.S. Cl. ................................ 540/145
[58] Field of Search ..................... 260/245.91

[56] References Cited

PUBLICATIONS

Scheer et al, JACS, vol. 97, No. 11 (1975), pp. 3273–3275.
Wasielewski et al, Tetrahedron Letters, No. 12 (1978), pp. 1043–1046.
McFeeters, Chemical Abstracts, vol. 82 (1975), 134838f.
Scheer et al, Tetrahedron, vol. 28 (1972), pp. 5839–5856.

Primary Examiner—Richard L. Raymond
Attorney, Agent, or Firm—William J. Daniel

[57] ABSTRACT

Nine-desoxo-hydroxy-pheophorbide derivatives and alkaline salts thereof represented by the general formula:

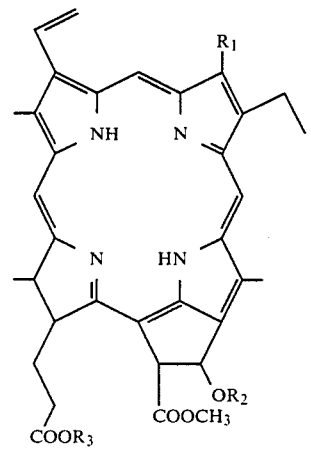

wherein
$R_1$ represents $CH_3$ or $CH_2OH$,
$R_2$ represents H or Ac, and
$R_3$ represents H or alkali metal, are useful for treating cancer having a strong preferential affinity for cancer cells over normal cells and exerting upon irradiation a destructive effect on such cancer cells.

1 Claim, 2 Drawing Figures

I —— PHYSIOLOGICAL SALINE   II ———— CANCER
III —··—··— LIVER   IV —···—···— KIDNEY
V ------- PLASMA

AFTER 24 HOURS

AFTER 48 HOURS

9-DESOXO-9-HYDROXY-PHEOPHORBIDE DERIVATIVES AND ALKALINE SALTS THEREOF

Nine-desoxo-9-hydroxy-pheophorbide derivatives and alkaline salts thereof represented by the general formula:

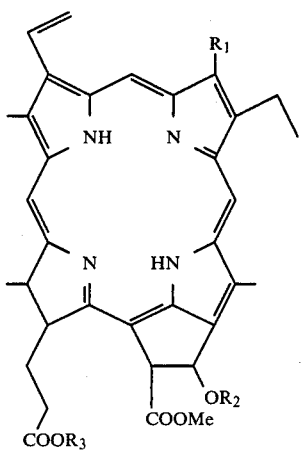

wherein
$R_1$ represents $CH_3$ or $CH_2OH$,
$R_2$ represents H or Ac, and
$R_3$ represents alkali metal such as H or Na and K.

FIELD OF THE INVENTION

The present invention relates to 9-desoxo-9-hydroxy-pheophorbide derivatives and their alkaline salts.

Compounds according to the present invention are novel and are not to be found in any publications. They have pharmacological effects such as photo-sensitivity and accumulative and destructive effects in cancer cells and are therefore very useful for medical purposes.

BACKGROUND OF THE INVENTION

In the treatment of cancers, particularly where porphine related compounds are used, combined use of laser beam with porphrine cobalt belonging to porphines derived from hemoglobin, mercury compounds, etc. or hematoporphyrin are being studied for practical use. However, the process for preparing these porphin compounds involves prolonged steps since animal blood (hemoglobin) which is limited in supply is processed first to obtain hemin, which is then converted to protoporphyrin. The supply of animal blood as the raw material is unstable, and it is extremely difficult to obtain protoporphyrin and hematoporphyrin derived from protoporphyrin with high purity. See Tetsuro CHO et al, Porphin no Kagaku, p. 47 Kyoritsu Shuppan, 1982.

The present inventors have long been engaged in the study of chlorophyll related compounds and applied for patent right on a highly economical process for separating and purifying pheophorbide in larger quantities which involves simple and brief operations and utilizes as the raw material photo-synthesized organisms that are available in stable supply at low cost. Japanese Laid-Open Patent Application Ser. No. 58-69884, filed Oct. 21, 1981.

On the hypothesis that phorbine compounds prepared from this pheophorbide have more intense physiological activities than porphines mentioned above, the present inventors continued their study and found for the first time that 9-desoxo-9-hydroxy-pheophorbide derivatives and their alkaline salts which are reduced products of pheophorbide (hereinafter referred to as the compounds of the present invention) have excellent pharmacological properties such as marked affinity to cancerous tissues, high photo-sensitivity and destructive effect on cancerous tissues that are superior to those observed in the above-identified porphines.

It has heretofore been known that porphine derivatives of hemoglobin origin are likely to be conjugated with cancerous tissues and are photo-sensitive. However, it has not been realized that phorbine derivatives of chlorophyll have similar physiological activities. In view of the circumstances, the inventors tried to synthesize various compounds from phorbine derivatives of chlorophyll, and after conducting screening tests on these substances, found that the compounds of the invention have pharmacological properties corresponding to those of porphine derivatives of hemoglobin, and thus succeeded in obtaining inexpensive and stable therapeutic agents for cancer to replace expensive and unstable porphines. It has also been discovered that acetyl derivatives of the present compounds in the form of their water soluble alkaline salts were gradually deacetylated in the aqueous solution to be released to 9-desoxo-9-hydroxy-pheophorbide exhibiting the pharmacological properties described above.

DETAILED DESCRIPTION OF THE INVENTION

Figure 1A:
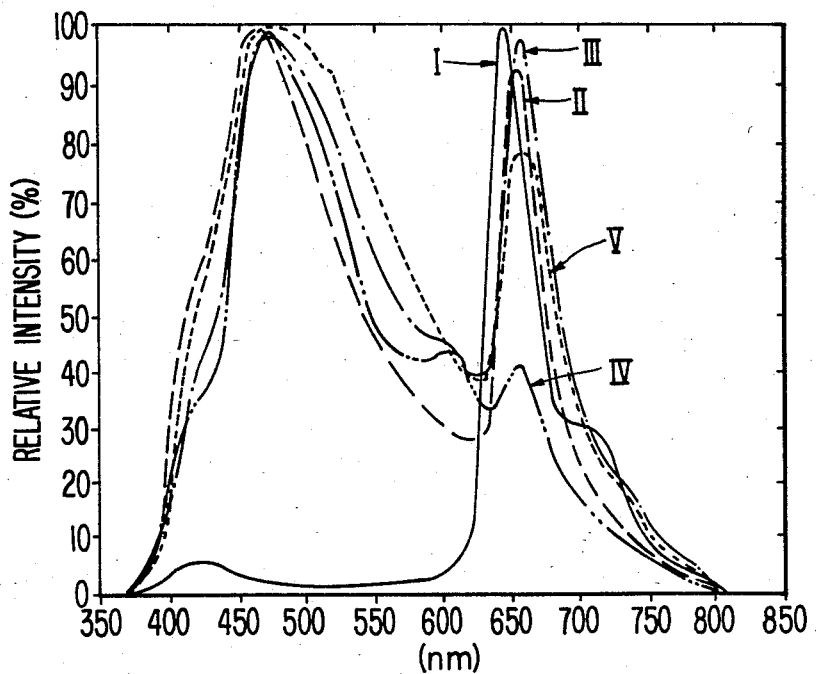
FIG. 1 is a graph showing the affinity of sodium 9-desoxo-9-hydroxy-pheophorbide to cancer cells in comparison to its affinity for liver and kidney cells and plasma and against a solution in saline for a control; and as measured by $N_2$ pulsed laser spectrofluorometry after 24 and 48 hours.

The present compounds are novel substances. Although there are cited in references the synthesis of analogous compounds such as 9-desoxo-9-hydroxy-pheophytin (M. R. Wasielewski et al, Tetrahedron Letters, 1043 (1978) and 9-desoxo-9-hydroxy-10-methoxy-methylpheophorbide (H. Scheer et al, Tetrahedron, 28, 5839 (1972)), these are different substances. Moreover, the aim of these authors was in the first instance to synthesize the compound as a part of their study in elucidating the mechanism of photo-synthesis in order to obtain compounds having an UV absorption profile more similar to that of chlorophyll P-700, and in the latter instance to synthesize various related derivatives to determine their absolute configuration, in order to investigate the influence of reaction conditions on yield and to publish data obtained from analyses and measurements by various devices. These references did not discuss physiological activities of the compounds on cancerous tissues which are the main object of the present invention. It has so far been unknown that the phorbine related compounds had such strong physiological activities, as observed in connection with this invention, which is understandable in view of the fact that no specific activity against cancer were found in the compounds from which the inventive compounds were derived, namely, pheophorbide and its alkaline salts and methyl pheophorbide.

The results of elemental analysis and nuclear magnetic resonance absorption of 9-desoxo-9-hydroxy-pheophorbide which is one of the present compounds are as follows:

Formula: $C_{35}H_{38}N_4O_5$; Calcd.: C, 70.69%: H, 6.44%: N, 9.42%; Found: C, 70.64%: H, 6.57%: N, 9.16%.

Nuclear magnetic resonance absorption ($^1$H-NMR) ($\delta$ ppm).

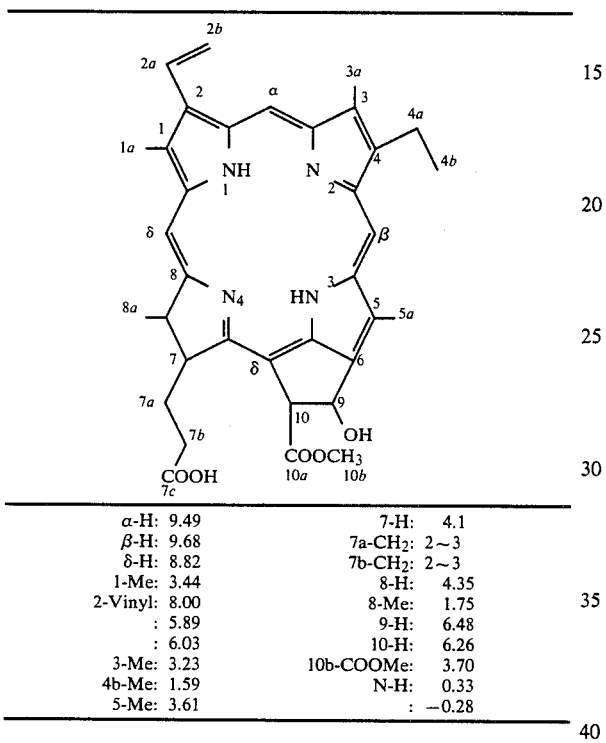

| α-H: 9.49 | 7-H: 4.1 |
|---|---|
| β-H: 9.68 | 7a-CH$_2$: 2~3 |
| δ-H: 8.82 | 7b-CH$_2$: 2~3 |
| 1-Me: 3.44 | 8-H: 4.35 |
| 2-Vinyl: 8.00 | 8-Me: 1.75 |
| : 5.89 | 9-H: 6.48 |
| : 6.03 | 10-H: 6.26 |
| 3-Me: 3.23 | 10b-COOMe: 3.70 |
| 4b-Me: 1.59 | N-H: 0.33 |
| 5-Me: 3.61 | : −0.28 |

Pharmacological activities of the present compounds will now be explained as compared with porphines. These substances become conjugated with cancerous tissue and react to light, generating singlet oxygen having intense oxidizing effect by which cancer cells are destroyed. By making use of this property, it is possible to treat not only the cancer projecting on the surface but also small cancer lesions in the mucous epithelium which are difficult to find and abnormal cells in a precancerous state.

There is not much difference between the present compounds and specific porphine-type substances as to their effect on cancer. However, while most porphine related compounds have strong photo-sensitivity, only a few have selective affinity to cancer cells. Without such selectivity, the substance is accumulated in other organs as well and proves to be photo-toxic to not only cancer cells but also to normal cells. In view of the above facts, there has been proposed a combined use of several porphines having selective affinity.

The present invention substances are of great utility as they are endowed with all the properties mentioned above (i.e., affinity to cancer cells, photo-sensitivity, destructive effect on cancer).

The process for preparing the compounds according to the present invention will now be described.

One of the present compounds is obtained by reducing pheophorbide (I) to produce 9-desoxo-9-hydroxy-pheophorbide (II). The reaction can be expressed by the following chemical formula:

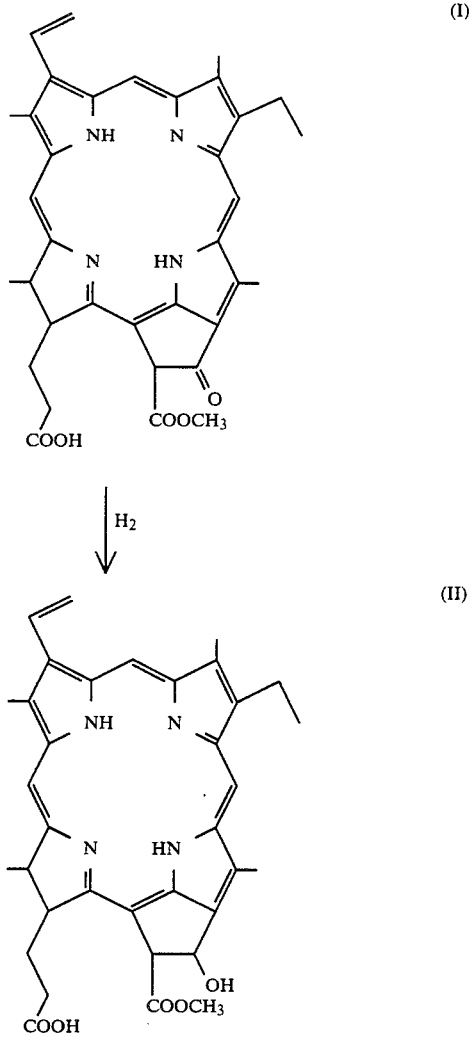

In practice, compound I is dissolved in a suitable solvent, i.e. methanol, and reacted with a suitable reducing agent such as NaBH$_4$.

A preferred result can be obtained by another preparation method of the present compounds, wherein pheophytin (III) or methyl pheophorbide (IV) is reduced in advance in a first step and the reaction product, 9-desoxo-9-hydroxy-pheophytin (V) or 9-desoxo-9-hydroxy-methyl pheophorbide (VI) is hydrolyzed in a second step.

A similarly preferable result can be obtained by still another process; compound I obtained through acid hydrolysis of compound III is similarly reduced to obtain compound II, or the latter (II) is acetylated to produce 9-desoxo-9-acetyloxy-pheophorbide (VII) (because when compound VII is an alkaline salt, it is released prior to compound II). Any combination of reactions other than those mentioned above may also be employed so long as they include hydrolysis, reduction and acetylation. It is also preferable but not essential to add a suitable antioxidant or solvent and heat the reaction system.

Although methanol, ethanol, acetonitrile, pyridine, etc. as solvents and $Na_2S_2O_3$, $Na_2S_2O_4$, ascorbic acid, etc. as reducing agents may be employed in preparing the present invention substances, the invention is not restricted to these solvents and reducing agents.

As mentioned above, the present invention utilizes as starting material photo-synthesized substances which are inexpensive and stably supplied. The process involves extremely simple operations which can be conducted in a short period of time to achieve isolation and synthesis. The present invention substances have physiological activities which are unique to phorbine related compounds and can be used per se as medical preparations, or offer unlimited use as the raw material for manufacturing other medicines. Unlike porphine derived from hemoglobin, they can be mass produced at higher purity and thus are extremely useful.

The pharmacological effects and preparation process of the present compounds will now be described by way of examples.

EXAMPLE 1

Laser irradiation to the removed organ (in vitro)

(A) $N_2$ pulsed laser spectrofluorometry

Five mg of the test drug sodium 9-desoxo-9-hydroxy pheophorbide diluted in physiological saline (1 ml) was IV administered (1 ml) to golden hamsters (5 each for a group) 14–21 days after transplantation of nitrosoamine-induced cancer cells of the pancreas, after which cancer cells and other organs were removed. $N_2$-pulsed laser ($N_2$ 337 nm, 2 ns 400–1000 nm) was irradiated to each organ thus obtained to measure $N_2$ pulsed laser spectrofluorometry. The result is shown in FIG. 1.

$N_2$ pulsed laser spectrofluorometry of each removed organ was measured 24 hours and 48 hours afterwards to investigate the wavelengths of 600 to 900 nm based on the peak wavelength of NADH of 470 nm.

Figure 1B:
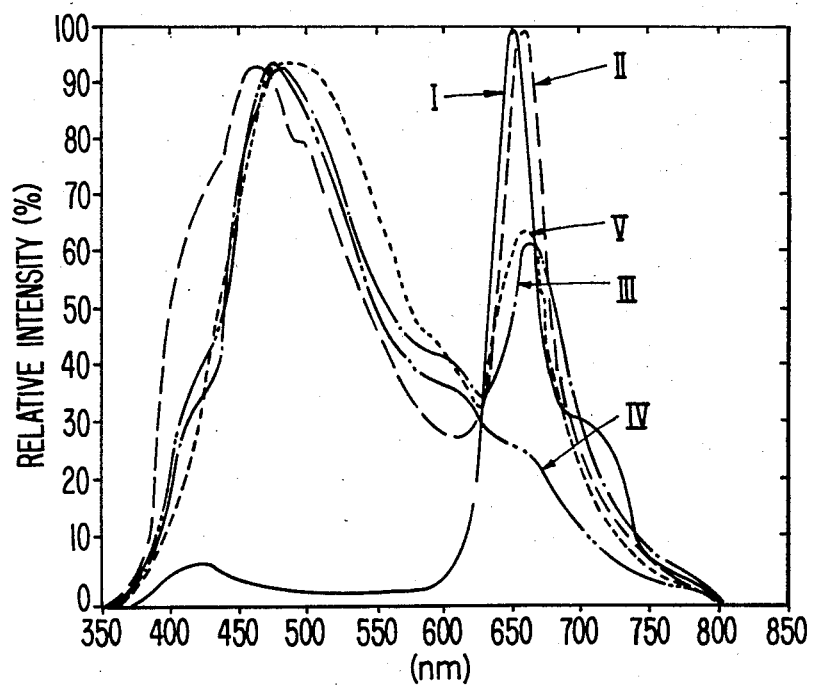

FIGS. 1a and b show, respectively, that although sodium 9-desoxo-9-hydroxy pheophorbide was generally found in organs after 24 hours, it had markedly accumulated in cancer cells alone but not in other cells after 48 hours.

As is obvious from the above result, sodium 9-desoxo-9-hydroxy pheophorbide was proved to have remarkable selective affinity to cancer cells.

(B) Biochemical luminescence by single photoncounter system

Sodium 9-desoxo-9-hydroxy pheophorbide dissolved in physiological saline of respective concentrations (25 μg/2 ml, 50 μg/2 ml, 100 μg/2 ml) was added to leukemic Molt 4 Cell ($1 \times 10^7$ Cells) and the resultant product was incubated for 24 hours at 37° C.

Each incubated cell thus obtained was irradiated with laser (He-Ne gas, 630 nm, 10 min, 20 mW) and trace biochemiluminescence was measured by single photoncounter system.

The intensity of biochemiluminescence substantially corresponds to the degree of destructive effect on cancer cells and thus by studying the biochemicluminescence by single photoncounter system, it is possible to predict the destructive effect on cancer cells.

Figure 2:
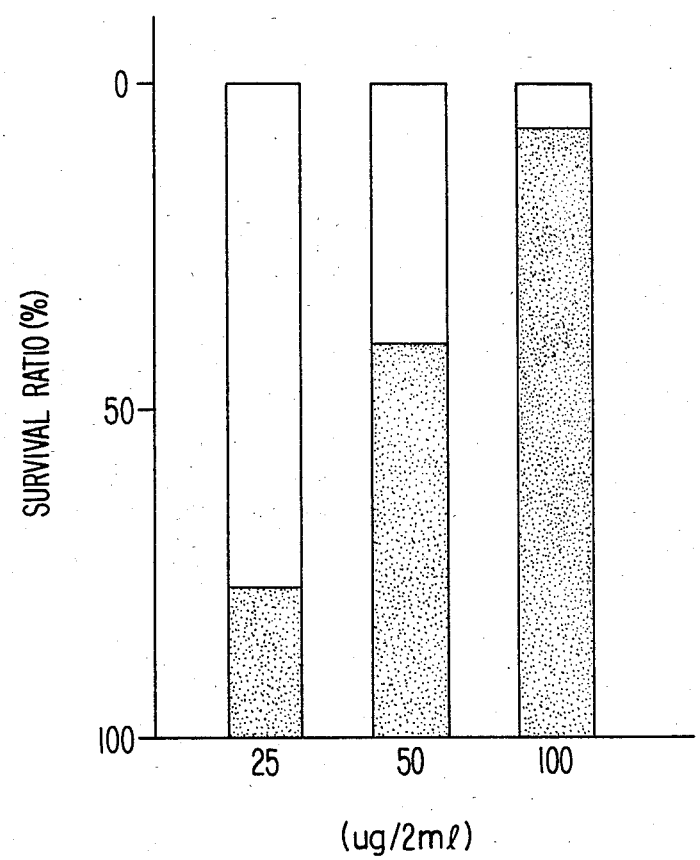
FIG. 2 is a graph showing the destructive effect of 9-desoxo-9-hydroxy-pheophorbide on cancer cells as measured by biochemiluminescence with a single photon-counter system.

FIG. 2 shows the intensity of biochemiluminescence and the destructive effect on cancer cells after laser irradiation. It is seen from FIG. 2 that more than 95% of the cancer cells were destroyed when the subject substance in the amount of 100 μg/2 ml was used.

The foregoing result shows that sodium 9-desoxo-9-hydroxy pheophorbide has intense photo-sensitivity and remarkable destructive effect on cancer cells.

Putting the above conclusion together, it is proved that remarkable affinity to cancerous tissues, intense photo-sensitivity and destructive effect on cancer cells are all found in sodium 9-desoxo-9-hydroxy pheophorbide.

EXAMPLE 2

Three grams of pheophorbide (I) was dissolved in 12 ml of pyridine and 60 ml of methanol into which 5% $NaBH_4$ solution was dropped under stirring. After the reaction was completed, crystals of 9-desoxo-9-hydroxy-pheophorbide (II) were precipitated when added with an aqueous solution of 5 % citric acid. These crystals were collected, washed with water and dried. (Yield 3 g). The yield was 98%.

Thus obtained compound II was dissolved in acetone and neutralized by adding 5 % $Na_2CO_3$ aqueous solution to obtain sodium 9-desoxo-9-hydroxy pheophorbide. The yield was 98%.

EXAMPLE 3

Three grams of methyl pheophorbide (IV) was dissolved in 70 ml of acetonitrile, added with aqueous solution of 5% $NaBH_4$ dropwise under stirring to obtain crude 9-desoxo-9-hydroxy-methyl pheophorbide (VI).

Thus obtained compound VI was suspended and dissolved in 40% $H_2SO_4$ aqueous solution and reacted for 1 hour under agitation. After the reaction was completed, 5% citric acid aqueous solution was added to the reaction liquid by a similar process to that used in Example 2 for the collection of compound II, and the crystalline product VI was washed with water and dried. The yield was 69%.

EXAMPLE 4

Fifty grams of crude chlorophyll (chlorophyll content 10%) was suspended and dissolved in 3-fold 50% $H_2SO_4$ aqueous solution, added with 0.5 g of $Na_2S_2O_3$, and reacted for 1 hour under agitation. A similar process to that in Example 3 was conducted to obtain compound I. Thus obtained compound I was further treated as in Example 2 to obtain compound II (yield 2.5 g). The yield (in proportion to crude chlorophyll used) was 7.6%.

EXAMPLE 5

One gram of compound II was acetylated with acetic anhydridepyridine by a conventional method to obtain 9-desoxo-9-acetyloxy-pheophorbide (VII) (yield 1 g). The yield was 99%.

Compound VII in an amount of 0.5 g was dissolved in ether and neutralized with 5% $Na_2CO_3$ aqueous solution to obtain sodium salt of 9-desoxo-9-acetyloxy-pheophorbide. The aqueous solution of this sodium salt was left standing for reaction to obtain 0.2 g of compound II. The yield was 40%.

We claim:

1. 9-desoxo-9-hydroxy-pheophorbide derivatives and alkaline salts thereof represented by the general formula:

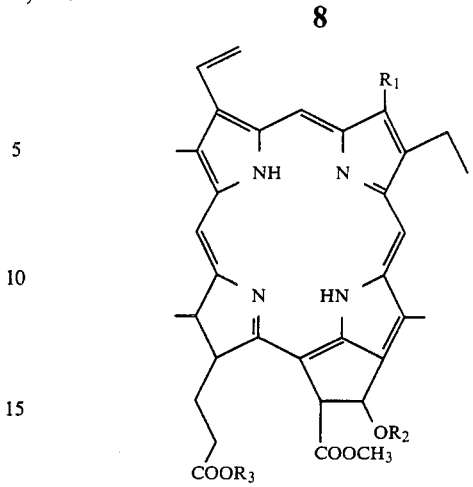
wherein
R$_1$ represents CH$_3$ or CH$_2$OH,
R$_2$ represents H or acetyl, and
R$_3$ represents H or an alkali metal atom.
* * * * *